(12) United States Patent
Liu et al.

(10) Patent No.: US 8,957,057 B2
(45) Date of Patent: Feb. 17, 2015

(54) USE OF AZAPHILONE COMPOUNDS FOR THE MODULATION OF THE ACTIVITY OF A NUCLEAR HORMONE RECEPTOR

(75) Inventors: Ta-Wei D. Liu, Hsinchu (TW); Yen-Lin Chen, Hsinchu (TW); Ming-Der Wu, Hsinchu (TW); Ming-Jen Cheng, Hsinchu (TW); Hui-Ping Chen, Hsinchu (TW); Wen-Jung Wu, Hsinchu (TW); Kai-Ping Chen, Hsinchu (TW); Yu-Shan Lin, Hsinchu (TW); Gwo-Fang Yuan, Hsinchu (TW)

(73) Assignee: Food Industry Research and Development Institute, Hsinchu (TW)

( * ) Notice: Subject to any disclaimer, the term of this patent is extended or adjusted under 35 U.S.C. 154(b) by 437 days.

(21) Appl. No.: 12/753,918

(22) Filed: Apr. 5, 2010

(65) Prior Publication Data

US 2010/0256227 A1 Oct. 7, 2010

Related U.S. Application Data

(60) Provisional application No. 61/166,787, filed on Apr. 6, 2009.

(51) Int. Cl.
  A01N 43/00 (2006.01)
  A61K 31/33 (2006.01)
  A61K 31/365 (2006.01)

(52) U.S. Cl.
  CPC .................. *A61K 31/365* (2013.01)
  USPC .......................... 514/183; 514/455

(58) Field of Classification Search
  USPC ........................................ 514/455
  See application file for complete search history.

(56) References Cited

U.S. PATENT DOCUMENTS 6,511,676 B1 * 1/2003 Boulikas ............... 424/450
7,378,426 B2 * 5/2008 Gavai et al. ........... 514/291

FOREIGN PATENT DOCUMENTS

JP 2008056618 A * 3/2008

OTHER PUBLICATIONS

Machine translation of JP2008056618.*
Sato et al, Journal of pediatric Surgery, vol. 38, No. 2, Feb. 2003, pp. 205-210.*
Hong et al, J. Med. Food 11 (4) Dec. 3, 2008, 657-666.*
Wild et al, J. Agric. Chem. 2002, 50, 3999-4002.*
Rosenhagen et al, Molecular & Endocrinology 17(10):1991-2001, 2003.*
Allan et al, Journal of Steroid and Biochemistry & Molecular Biology 103 (2007) 76-83.*
Tsuji, K., et al., 1992, "Effects of two kinds of Koji on blood pressure in spontaneously hypertensive rats." Nippon. Nogeikagaku Kaishi., 66: 1241-1246.
Endo, A., 1979, "Monacolin K, a new hypocholesterolemic agent produced by a Monascus species." J. Antbiot., 32: 852-854.
Endo, A., 1985, "Compactin (ML-236B) and related compounds as potential cholesterol-lowering agents that inhibit HMG-CoA reductase." J. Med. Chem., 28: 401-405.
Martinokova, L., et al., 1995, "Biological activity of polykedite pigments produced by the fungus Monascus." J. Appl. Bacteriol., 79: 609-616.
Wong, H. C. and Bau, Y. S., 1977, "Pigmentation and Antibacterial Activity of Fast Neutron- and X-Ray-induced Strains of Monascus purpureus Went." Plant Physiol., 60: 578-581.
Ma, J., et al., 2000, "Constituents of red yeast rice, a traditional Chinese food and medicine." J. Agric. Food Chem., 48: 5220-5225.
Nozaki, H., et al., 1991, "Ankalactone, a new ?,?-unsaturated ?-lactone from Monascus anka." Agric. Biol. Chem., 55: 899-900.
Blanc, P. J., et al., 1995, "Production of citrinin by various species of Monascus." Biotechnol. Lett., 17: 291-294.
Juzlová, P., et al., 1996, Secondary metabolites of the fungus Monascus: a review. J. Industrial Microbiol., 16: 163-170.
Sato, K., et al., 1997, "Identification of major pigments containing D-amino acid units in commercial Monascus pigments." Chem. Phann. Bull., 45: 227-229.
Wild, D., et al., 2002, "New Monascus metabolite isolated from red yeast rice (angkak, red koji)." J. Agric. Food Chem., 50: 3999-4002.
Wild, D., et al., 2003, "New Monascus metabolites with a pyridine structure in red fermented rice." J. Agric. Food Chem., 51:5493-5496.

(Continued)

*Primary Examiner* — Wu-Cheng Winston Shen
*Assistant Examiner* — Jean Cornet
(74) *Attorney, Agent, or Firm* — Ladas & Parry LLP

(57) ABSTRACT

The present invention concerns the uses of an azaphilone compound of formula (I):
formula (I):

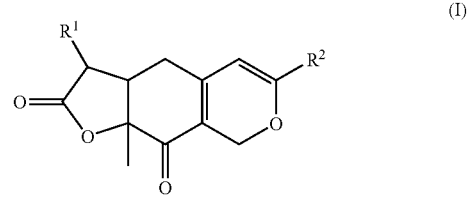

or a pharmaceutically acceptable derivative thereof as described in the specification for modulation of the activity of a nuclear hormone receptor and for prevention and/or treatment of a disease or disorder related to nuclear hormone receptor activity.

9 Claims, 12 Drawing Sheets

(56) References Cited

OTHER PUBLICATIONS

Akihisa, T., et al., 2004, "(+)- and (-)-syn-2-isobutyl-4-methylazetidine-2,4- dicarboxylic acids from the extract of Monascus pilosus-fermented rice (red-mold rice)." J. Nat. Prod., 67: 479-480.

Jongrungruangchok, S., et al., 2004, "Azaphilone pigments from a yellow mutant of the fungus Monascus kaoliang." Phytochemistry, 65: 2569-2575.

Akihisa, T., et al., 2005, "Azaphilones, furanoisophthalides, and amino acids from the extracts of Monascus pilosus-fermented rice (red-mold rice) and their chemopreventive effects." J. Agric. Food Chem., 53: 562-565.

Campoy, S. et al., 2006, "Characterization of a hyperpigmenting mutant of Monascus purpureus IB 1: identification of two novel pigment chemical structures." Appl. Microbiol. Biotechnol. 70: 488-496.

Cabeza, M., et al., 2001, "Evaluation of new pregnane derivatives as 5alpha-reductase inhibitor." Chem. Pharm. Bull. (Tokyo), 49(5): 525-30.

Matsuda, H., et al., 2001, "Anti-androgenic activity of Myricae Cortex—isolation of active constituents from bark of Myrica rubra." Biol. Pharm. Bull., 24(3): 259-63.

Alley, M.C., et al., 1988, "Feasibility of Drug Screening with Panels of Human Tumor Cell Lines Using a Microculture Tetrazolium Assay." Cancer Research, 48: 589-601.

Shang, et al., Cytotoxic Steroids From Monascus Purpureus-fermented Rice, Steroids 76 (2011) pp. 1185-1189.

Sato, et al., Expression of PPAR-Gamma Is Correlated With the Clinical Course of Neuroblastoma, Journal of Pediatric Surgery, vol. 38, No. 2 (Feb.), 2003; pp. 205-210.

Alderden, et al., The Discovery and Development of Cisplatin, Journal of Chemical Education, vol. 83, No. 5, May 2006.

* cited by examiner

USE OF AZAPHILONE COMPOUNDS FOR THE MODULATION OF THE ACTIVITY OF A NUCLEAR HORMONE RECEPTOR

This application claims the benefit of U.S. Provisional Application 61/166,787 filed Apr. 6, 2009, and incorporates the same by reference.

FIELD OF THE INVENTION

The present invention relates to compositions comprising an azaphilone compound, and the use of an azaphilone compound for modulation of the activity of a nuclear hormone receptor and for prevention and/or treatment of a disease or disorder related to nuclear hormone receptor activity.

BACKGROUND OF THE INVENTION

*Monascus* has been used in Oriental fermented foods for thousands of years. Red yeast rice fermented with *Monascus* spp. produces bioactive metabolites such as γ-aminobutyric acid (GABA), polyketides monacolin K, and some pigments, which respectively function as an anti-hypertension agent (see Tsuji, K., et al., 1992, "Effects of two kinds of Koji on blood pressure in spontaneously hypertensive rats." *Nippon. Nogeikagaku Kaishi.*, 66: 1241-1246), a cholesterol-lowering drug (see Endo, A., 1979, "Monacolin K, a new hypocholesterolemic agent produced by a *Monascus* species." *J. Antbiot.*, 32: 852-854; Endo, A., 1985, "Compactin (ML-236B) and related compounds as potential cholesterol-lowering agents that inhibit HMG-CoA reductase." *J. Med. Chem.*, 28: 401-405; and Martinokova, L., et al., 1995, "Biological activity of polykedite pigments produced by the fungus *Monascus*." *J. Appl. Bacteriol.*, 79: 609-616), and possess antibacterial activity (see Wong, H. C. and Bau, Y. S., 1977, "Pigmentation and Antibacterial Activity of Fast Neutron- and X-Ray-induced Strains of *Monascus purpureus* Went." *Plant Physiol.*, 60: 578-581). *Monascus* pigments, secondary metabolites possessing mainly azaphilone skeletons, have traditionally been used as natural food colorants (see Ma, J., et al., 2000, "Constituents of red yeast rice, a traditional Chinese food and medicine." *J. Agric. Food Chem.*, 48: 5220-5225). Many other metabolites have also been reported in previous research, see, for example, Nozaki, H., et al., 1991, "Ankalactone, a new α,β-unsaturated γ-lactone from *Monascus anka*." *Agric. Biol. Chem.*, 55: 899-900; Blanc, P. J., et al., 1995, "Production of citrinin by various species of *Monascus*." *Biotechnol. Lett.*, 17: 291-294; Juzlová, P., et al., 1996, "Secondary metabolites of the fungus *Monascus*: a review. *J. Industrial Microbiol.*, 16: 163-170; Sato, K., et al., 1997, "Identification of major pigments containing D-amino acid units in commercial *Monascus* pigments." *Chem. Pharm. Bull.*, 45: 227-229; Wild, D., et al., 2002, "New *Monascus* metabolite isolated from red yeast rice (angkak, red koji)." *J. Agric. Food Chem.*, 50: 3999-4002; Wild, D., et al., 2003, "New *Monascus* metabolites with a pyridine structure in red fermented rice." *J. Agric. Food Chem.*, 51:5493-5496; Akihisa, T., et al., 2004, "(+)- and (−)-syn-2-isobutyl-4-methylazetidine-2,4-dicarboxylic acids from the extract of *Monascus pilosus*-fermented rice (red-mold rice)." *J. Nat. Prod.*, 67: 479-480; Jongrungruangchok, S., et al., 2004, "Azaphilone pigments from a yellow mutant of the fungus *Monascus kaoliang*." *Phytochemistry*, 65: 2569-2575; and Akihisa, T., et al., 2005, "Azaphilones, furanoisophthalides, and amino acids from the extracts of *Monascus pilosus*-fermented rice (red-mold rice) and their chemopreventive effects." *J. Agric. Food Chem.*, 53: 562-565). Most of them were isolated from red yeast rice obtained from solid fermentation. There is still a need to discover new constituents in red yeast rice and their potential applications.

SUMMARY OF THE INVENTION

One of the purposes of the invention is to provide a composition comprising the compound of formula (I):

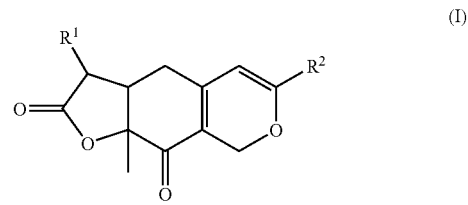

or a pharmaceutically acceptable derivative thereof, and optionally a pharmaceutically acceptable carrier or excipient, wherein $R^1$ is —CH(OH)-alkyl or —C(O)-alkyl and $R^2$ is alkenyl.

Another purpose of the present invention is to provide a method for modulating the activity of a nuclear hormone receptor in a subject in need of such modulation.

A further purpose of the present invention is to provide a method for modulating the activity of 5α-reductase in a subject in need of such modulation.

The present invention also relates to a method for preventing and/or treating a disease or disorder related to androgen activity in a subject.

The present invention is described in detail in the following sections. Other characteristics, purposes and advantages of the present invention can be easily found in the detailed descriptions and claims.

DETAILED DESCRIPTION OF THE INVENTION

Figure 1:
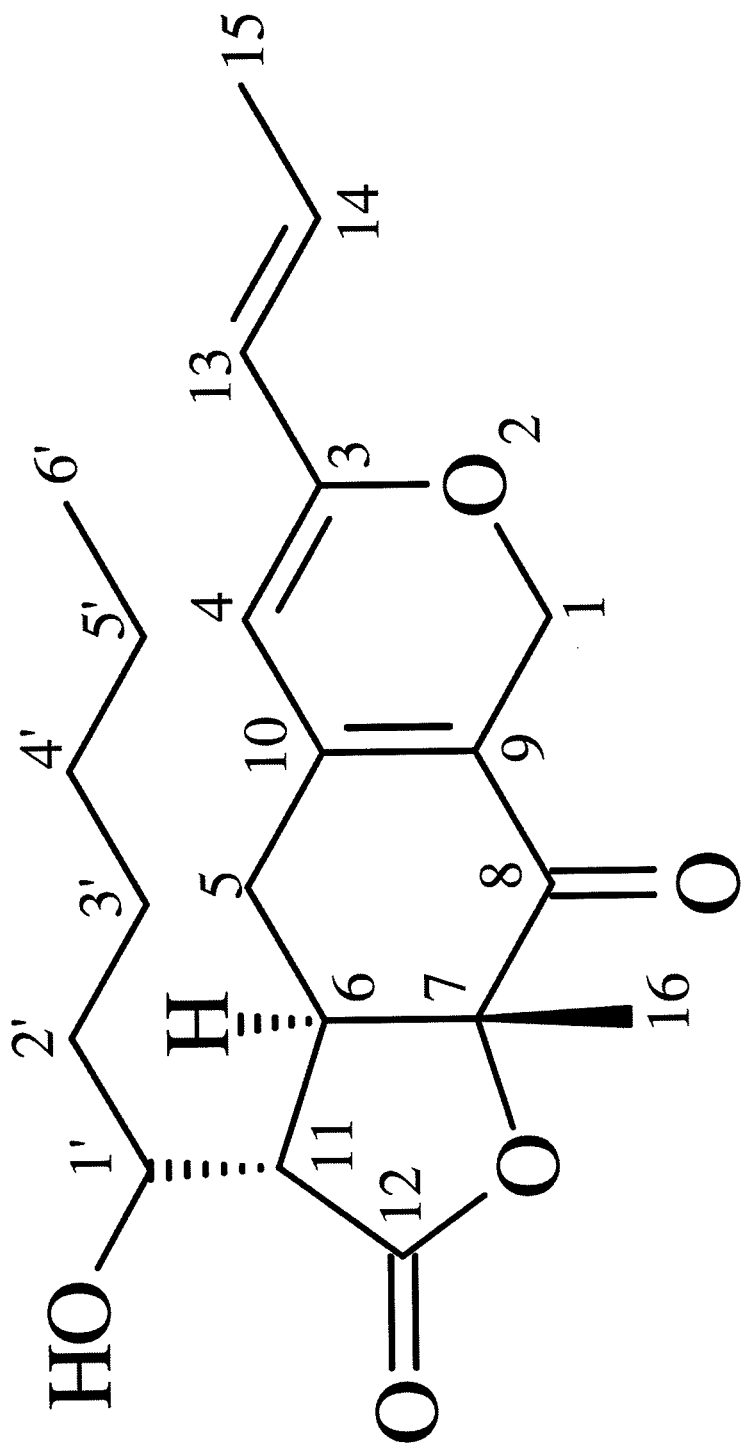
FIG. 1 shows the structure of monascuspiloin.

The present invention can be understood more readily by reference to the following detailed description of various embodiments of the invention and the examples included therein and to the chemical drawings and tables and their previous and following descriptions. Before the present compounds, compositions, and/or methods are disclosed and described, it is to be understood that unless otherwise specifically indicated by the claims, the invention is not limited to specific preparation methods, specific carriers or formulations, or to particular modes of formulating the compounds of the invention into products or compositions intended for topical, oral or parenteral administration, because as one of ordinary skill in relevant arts is well aware, such things can, of course, vary. It is also to be understood that the terminology used herein is for the purpose of describing particular embodiments only and is not intended to be limiting.

Definitions

As utilized in accordance with the present disclosure, the following terms, unless otherwise indicated, shall be understood to have the following meanings:

The term "isolated" or "isolation" means that the material is removed from its original environment (e.g., the natural environment if it is naturally existing). The term "isolated" does not necessarily reflect the extent to which the material has been purified.

The term "mutant" or "variant" is meant to encompass any microorganism whose total cellular genetic composition has been altered, for example, by chemical mutagenesis, spontaneous mutation, genetic engineering, transformation, or transfection, so that its physical or biochemical properties are affected. For example, the variant or mutant may have all the identifying characteristics of *Monascus pilosus* BCRC 31523, *Monascus lunisporus* BCRC 33640, *Monascus ruber* BCRC 31523, *Monascus ruber* BCRC 31535 or *Monascus pilosus* BCRC 33947.

The term "an azaphilone compound" or "azaphilone compounds" as used herein denotes a compound that possesses mainly an azaphilone structure.

As used herein, the terms "alkyl" and "alkenyl" include straight and branched chains.

"Alkyl" refers to a hydrocarbon group that can be conceptually formed from an alkane by removing hydrogen from the structure of a non-cyclic hydrocarbon compound having straight or branched carbon chains, and replacing the hydrogen atom with another atom or organic or inorganic substituent group. In some embodiments of the invention, the alkyl groups are "$C_1$ to $C_{10}$ alkyl" such as methyl, ethyl, propyl, isopropyl, n-butyl, iso-butyl, sec-butyl, tert-butyl, amyl, tert-amyl, hexyl and the like. Many embodiments of the invention comprise "$C_1$ to $C_7$ alkyl" groups that include methyl, ethyl, propyl, iso-propyl n-butyl, iso-butyl, sec-butyl, t-butyl, pentyl, hexyl, and heptyl groups.

The term "alkenyl" is structurally analogous to an alkyl group or residue that comprises at least one carbon-carbon double bond. In some embodiments, the alkenyl groups are "$C_2$ to $C_7$ alkenyls" which are exemplified by vinyl, allyl, propenyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, and 6-heptenyl, as well as dienes and trienes of straight and branched chains. In other embodiments, alkenyls are limited to two to four carbon atoms.

The term "a pharmaceutically acceptable derivative" or "pharmaceutically acceptable derivatives" as used herein denotes a compound that is modified from the compound of the invention but has properties and efficacies that are the same as or better than those of the compound of the invention. Preferably, the pharmaceutically acceptable derivative is a pharmaceutically acceptable salt, solvate or prodrug of the compound of the invention.

One or more of the compounds of the invention, may be present as a salt. The term "salt" encompasses those salts formed with the organic and inorganic anions and cations. Furthermore, the term includes salts that form by standard acid-base reactions with basic groups and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and like acids.

The compounds of the invention can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

The term "subject" as used herein denotes any animal, preferably a mammal, and more preferably a human. Examples of subjects include humans, non-human primates, rodents, guinea pigs, rabbits, sheep, pigs, goats, cows, horses, dogs and cats.

The term "effective amount" of a compound as provided herein means a sufficient amount of the compound to provide the desired regulation of a desired function, such as gene expression, protein function, or the induction of a particular type of response. As will be pointed out below, the exact amount required will vary from subject to subject, depending on the disease state, physical conditions, age, sex, species and weight of the subject, specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount."However, an appropriate effective amount can be determined by one of ordinary skill in the art using only routine experimentation.

The term "preventing" or "prevention" is recognized in the art, and when used in relation to a condition, it includes administering, prior to onset of the condition, an agent to reduce the frequency or severity of or delay the onset of symptoms of a medical condition in a subject relative to a subject which does not receive the agent.

The term "treating" or "treatment" as used herein denotes reversing, alleviating, inhibiting the progress of, or improving the disorder or condition to which such term applies, or one or more symptoms of such disorder or condition.

The term "carrier" or "excipient" as used herein refers to any substance, not itself a therapeutic agent, used as a carrier and/or diluent and/or adjuvant, or vehicle for delivery of a therapeutic agent to a subject or added to a formulation to improve its handling or storage properties or to permit or facilitate formation of a dose unit of the composition into a discrete article such as a capsule or tablet suitable for oral administration. Suitable carriers or excipients are well known to persons of ordinary skill in the art of manufacturing pharmaceutical formulations or food products. Carriers or excipients can include, by way of illustration and not limitation, buffers, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable carriers or excipients include citrate buffer, phosphate buffer, acetate buffer, bicarbonate buffer, stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials (such as cellulose esters of alkanoic acids and cellulose alkyl esters), low melting wax cocoa butter, amino acids, urea, alcohols, ascorbic acid, phospholipids, proteins (for example, serum albumin), ethylenediamine tetraacetic acid (EDTA), dimethyl sulfoxide (DMSO), sodium chloride or other salts, liposomes, mannitol, sorbitol, glycerol or powder, polymers (such as polyvinyl-pyrrolidone, polyvinyl alcohol, and polyethylene glycols), and other pharmaceutically acceptable materials. The carrier should not destroy the pharmacological activity of the therapeutic agent and should be non-toxic when administered in doses sufficient to deliver a therapeutic amount of the agent.

Often, ranges are expressed herein as from "about" one particular value and/or to "about" another particular value. When such a range is expressed, another embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to the other endpoint and independently of the other endpoint.

"Optional" or "optionally" means that the subsequently described event or circumstance may or may not occur, and that the description includes instances where said event or circumstance occurs and instances where it does not. For example, the phrase "optionally comprise an agent" means that the agent may or may not exist.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

The Compounds of the Invention

The present invention relates to azaphilone compounds. The azaphilone compounds of the invention have the following formula (I):

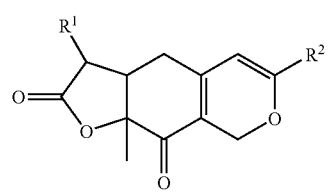

wherein $R^1$ is —CH(OH)-alkyl or —C(O)-alkyl or —C(O)-alkyl and $R^2$ is alkenyl.

In some embodiments of the compound of formula (I), $R^1$ is —CH(OH)—$C_1$-$C_{10}$alkyl, preferably —CH(OH)—$C_5$-$C_7$alkyl, and $R^2$ is $C_2$-$C_7$alkenyl, preferably $C_2$-$C_4$alkenyl.

In a preferred embodiment, $R^1$ is —CH(OH)-pentyl and $R^2$ is propenyl.

In some embodiments of the compound of formula (I), $R^1$ is —C(O)—$C_1$-$C_{10}$alkyl, preferably —C(O)—$C_5$-$C_7$alkyl, and $R^2$ is $C_2$-$C_7$alkenyl, preferably $C_2$-$C_4$alkenyl.

In a preferred embodiment, $R^1$ is —C(O)-pentyl and $R^2$ is propenyl.

In another preferred embodiment, $R^1$ is —C(O)-heptyl and $R^2$ is propenyl.

In another preferred embodiment, the compound of formula (I) is

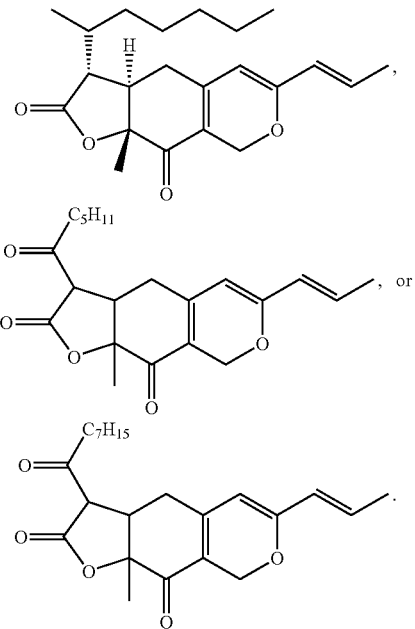

In a most preferred embodiment, the compound of formula (I) is (3S,3aR,9aR)-3a,4-dihydro-3-((S)-1-hydroxyhexyl)-9a-methyl-6-((E)-prop-1-enyl)-3H-furo [3, 2-g]isochromene-2,9(8H,9aH)-dione.

The compounds of the invention can be further converted into a pharmaceutically acceptable derivative, such as a pharmaceutically acceptable salt, solvate or prodrug, by any known methods.

The Compositions of the Invention

The present invention also provides a composition comprising the compound of the invention or a pharmaceutically acceptable derivative thereof. The composition of the invention can be a food composition or a pharmaceutical composition. The compound of formula (I) of the present invention presented in the composition can be provided in the form of a chemical compound, or a red yeast rice fermentation product of Monascus spp. or extract thereof comprising the compound.

The pharmaceutical composition of the invention can be administered topically or systemically by any method known in the art, including, but not limited to, intramuscular, intradermal, intravenous, subcutaneous, intraperitoneal, intranasal, oral, mucosal or external routes. The appropriate route, formulation and administration schedule can be determined by those skilled in the art. In the present invention, the pharmaceutical composition can be formulated in various ways, according to the corresponding route of administration, such as a liquid solution, a suspension, an emulsion, a syrup, a tablet, a pill, a capsule, a sustained release formulation, a powder, a granule, an ampoule, an injection, an infusion, a kit, an ointment, a lotion, a liniment, a cream or a combination thereof. If necessary, it may be sterilized or mixed with any pharmaceutically acceptable carrier or excipient, many of which are known to one of ordinary skill in the art, see paragraph [0035] for example.

The Preparation Processes of the Invention

In one preferred embodiment, the process for producing the compound of formula (I) comprises the steps of:

(a) fermenting rice with an isolated *Monascus* spp. to obtain red yeast rice;

(b) drying the red yeast rice and extracting the dried red yeast rice with 100% ethanol; and (c) purifying the ethanol extract of (b) with HPLC to obtain the compound.

According to the process of the invention, the isolated *Monascus* spp. can be any species that can produce the compound of formula (I), for example, *Monascus lunisporus* BCRC 33640, *Monascus ruber* BCRC 31523, *Monascus ruber* BCRC 31535 and *Monascus pilosus* BCRC 33947 obtained from the Food Industry Research and Development Institute (FIRDI), 331 Shih-Pin Road, 300, Hsinchu, Taiwan, R.O.C. These strains can also be obtained from the international deposit authorities. For example, *Monascus ruber* BCRC 31523 is also available from National Institute of Technology and Evaluation (NITE) Biological Research Center (NBRC), Japan, as NBRC 4483.)

In another preferred embodiment, the process of the invention comprises the steps of:

a) reacting a compound of formula (II):

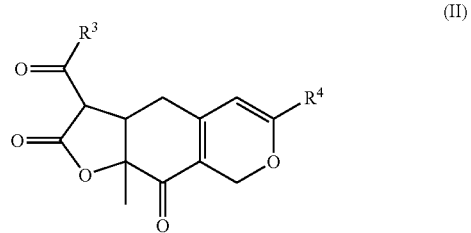

(II)

wherein $R^3$ is alkyl or —C(O)-alkyl and $R^4$ is alkenyl, with a sodium borohydride at 0° C. to form a compound of formula (I):

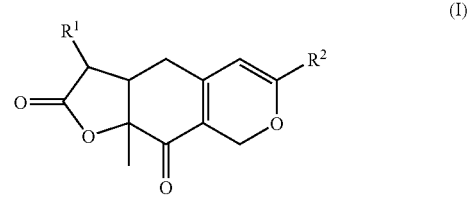

(I)

wherein $R^1$ is —CH(OH)-alkyl or —C(O)-alkyl and $R^2$ is alkenyl, and b) optionally converting the compound of formula (I) into a pharmaceutically acceptable derivative.

Utilities

The compound of formula I of the present invention can be used as a yellow pigment for foods or medicaments. The present invention surprisingly found that an azaphilone compound was capable of inhibiting the activity of a nuclear hormone receptor and 5α-reductase.

Nuclear hormone receptors are a class of proteins found within the interior of cells and are responsible for sensing the presence of hormones and certain other molecules. In response, these receptors work in concert with other proteins to regulate the expression of specific genes, thereby controlling the development, homeostasis, and metabolism of the organism.

An androgen receptor (AR) is a type of nuclear hormone receptor which is activated by binding of either of the androgenic hormones testosterone or dihydrotestosterone. The main function of an androgen receptor is as a DNA binding transcription factor that regulates gene expression. However, the androgen receptor has additional functions independent of DNA binding. The androgen receptor is most closely related to the progesterone receptor, and thus, progestins in higher dosages can block the androgen receptor.

The over-expression of an androgen receptor, or expression of mutated androgen receptor genes, has been found in several diseases, such as cancer, including prostate cancer and breast cancer, as well as other disorders such as polyglutamate disease, androgen-dependent alopecia, hirsutism, acne, prostatic hyperplasia, spinal and muscular atrophy and Kennedy's disease.

5α-reductase is an enzyme that converts testosterone, an androgen, into the more potent dihydro-testosterone (DHT). Androgens are part of the biology of gender and stimulate and control the development and maintenance of masculine characteristics. DHT is 3 times more potent than testosterone, while testosterone is 5-10 times more potent than adrenal androgens.

DHT is the primary contributing factor in male-pattern baldness. This is not the case for women. Women with increased levels of DHT may develop certain androgynous male secondary sex characteristics, including a deepened voice and facial hair. DHT may play a role in the development or exacerbation of benign prostatic hyperplasia and prostate cancer, by enlarging the prostate gland. DHT is also known to participate in the development of acne in some cases.

The present invention thus provides the following therapeutic methods.

One aspect of the therapeutic method of the present invention is to modulate the activity of a nuclear hormone receptor in a subject in need of such modulation, which comprises administering to said subject an effective amount of a compound of formula (I) or a pharmaceutically acceptable derivative thereof, or a red yeast rice fermentation product of *Monascus* spp. or extract thereof comprising the compound.

In some embodiments, the nuclear hormone receptor to be modulated is chosen from an androgen receptor, a glucocorticoid receptor, a progesterone receptor and an estrogen receptor. In one preferred embodiment, the nuclear hormone receptor is an androgen receptor.

In certain embodiments, the $IC_{50}$ of the compounds of formula (I) for the inhibition of a nuclear hormone receptor is from about 10 µM to about 50 µM, preferably from about 12 µM to about 35 µM.

Another aspect of the therapeutic method of the present invention is to prevent and/or treat a disease or disorder related to nuclear hormone receptor activity in a subject, which comprises administering to said subject an effective amount of a compound of formula (I) or a pharmaceutically acceptable derivative thereof, or a red yeast rice fermentation product of *Monascus* spp. or extract thereof comprising the compound.

In some embodiments, the nuclear hormone receptor to be modulated is chosen from an androgen receptor, a glucocorticoid receptor, a progesterone receptor and an estrogen receptor. In one preferred embodiment, the nuclear hormone receptor is an androgen receptor.

In certain embodiments, the disease or disorder related to nuclear hormone receptor activity is a disease or disorder related to over-activation of androgen receptors or expression of mutated androgen receptor genes, such as prostate cancer, prostatic hyperplasia, androgen-dependent alopecia, hirsutism, acne and other hyper-androgenic syndromes.

Another aspect of the therapeutic method of the present invention is to modulate the activity of 5α-reductase in a subject in need of such modulation, which comprises administering to said subject an effective amount of a compound of formula (I) or a pharmaceutically acceptable derivative thereof, or a red yeast rice fermentation product of *Monascus* spp. or extract thereof comprising the compound.

In certain embodiments, the $IC_{50}$ of the compounds of formula (I) for the inhibition of a nuclear hormone receptor is from about 200 µM to about 400 µM, preferably from about 300 µM to about 350 µM, and more preferably from about 320 µM to about 325 µM.

Still another aspect of the therapeutic method of the present invention is to prevent and/or treat a disease or disorder related to androgen receptor activity in a subject, which comprises administering to said subject an effective amount of a compound of formula (I) or a pharmaceutically acceptable derivative thereof, or a red yeast rice fermentation product of *Monascus* spp. or extract thereof comprising the compound.

In certain embodiments, the disease or disorder related to androgen receptor activity is chosen from prostate cancer, prostatic hyperplasia, androgen-dependent alopecia, hirsutism, acne and other hyper-androgenic syndromes.

According to the methods of the present invention, the compounds of formula (I') or a pharmaceutically acceptable derivative thereof can be administered topically or systemically by any method known in the art, including, but not limited to, intramuscular, intradermal, intravenous, subcutaneous, intraperitoneal, intranasal, oral, mucosal or external routes. The appropriate route, formulation and administration schedule can be determined by those skilled in the art.

According to the methods of the present invention, the compounds of formula (I) or a pharmaceutically acceptable derivative thereof, or the red yeast rice fermentation product of *Monascus* spp. or extract thereof comprising the compound can be administered in combination with a second agent effective in preventing and/or treating prostate cancer, prostatic hyperplasia, androgen-dependent alopecia, hirsutism, acne and other hyper-androgenic syndromes, thereby improving the therapeutic effect of the compounds of formula (I) or a pharmaceutically acceptable derivative thereof. Many agents are known in the art to be effective in preventing and/or treating prostate cancer, prostatic hyperplasia, androgen-dependent alopecia, hirsutism, acne and other hyper-androgenic syndromes. Examples of such agents include, but are not limited to, flutamide, bicalutamide, nilutamide, cyproterone acetate, ketoconazole, aminoglutethimide, abarelix, leuprolide, goserelin, triptorelin, buserelin, abiraterone acetate, doxazosin, terazosin, alfuzosin, tamsulosin, bactericidals, antibiotics, and retinoids.

The following examples are provided to aid those skilled in the art in practicing the present invention.

EXAMPLES

Example 1

Preparation of Red Yeast Rice

Zailai rice (long grain rice) was soaked in 0.2% tartaric acid solution at 4° C. overnight. Then, the liquid was drained off and the rice was sterilized at 121° C. for 15 minutes.

Each of *Monascus lunisporus* strain BCRC 33640, *Monascus ruber* strain BCRC 31523, *Monascus ruber* strain BCRC 31535 and *Monascus pilosus* strain BCRC 33947 was inoculated on a Potato Dextrose Agar (PDA) (Difco, USA) plate and incubated at 30° C. for 7 days. The spores were washed out from the PDA plate using sterile water and the concentration of the spore suspension was diluted to $1 \times 10^6$/ml.

5 g of the sterile Zailai rice were put in a 50- ml tube and mixed with 1 ml of the spore suspension of each strain and 1 ml of sterile water. The rice was incubated at 25° C. and left still for 21 days so as to obtain a red yeast rice fermentation product.

The red yeast rice fermentation products were dried and 1 g of each dried red yeast rice fermentation product was extracted with 100% EtOH (10 ml) for 24 hours. The ethanol extracts were examined by HPLC and found that the amounts of Compound 1 in the dried fermentation products of *Monascus lunisporus* BCRC 33640, *Monascus ruber* BCRC 31523, *Monascus ruber* BCRC 31535, and *Monascus pilosus* BCRC 33947 were 0.02, 0.31, 0.20, and 0.30 mg/g, respectively.

Example 2

Characterization of Compound 1 (Monascuspiloin)

Optical rotations were measured on a Jasco P-1020 digital polarimeter. UV spectra were obtained on a Jasco UV-240 spectrophotometer in MeOH, and IR spectra (KBr or neat) were taken on a Perkin-Elmer System 2000 FT-IR spectrometer. 1D ($^1H$, $^{13}C$, DEPT) and 2D (COSY, NOESY, HSQC, HMBC) NMR spectra using $CDCl_3$ and $CD_3OD$ as solvent were recorded on a Varian Unity Plus 400 (400 MHz for $^1H$ NMR, 100 MHz for $^{13}C$ NMR) and Varian INOVA-500 (500 MHz for $^1H$ NMR, 125 MHz for $^{13}C$ NMR) spectrometer. Chemical shifts were internally referenced to the solvent signals in $CDCl_3$ ($^1H$, δ7.26; $^{13}C$, δ77.0) with TMS as the internal standard. Low-resolution ESI-MS spectra were obtained on an API 3000 (Applied Biosystems) and high-resolution ESI-MS spectra on a Bruker Daltonics APEX II 30e spectrometer. Silica gel (70-230, 230-400 mesh) (Merck) was used for column chromatography, and silica gel 60 F-254 (Merck) was used for TLC and preparative TLC.

Figure 2:
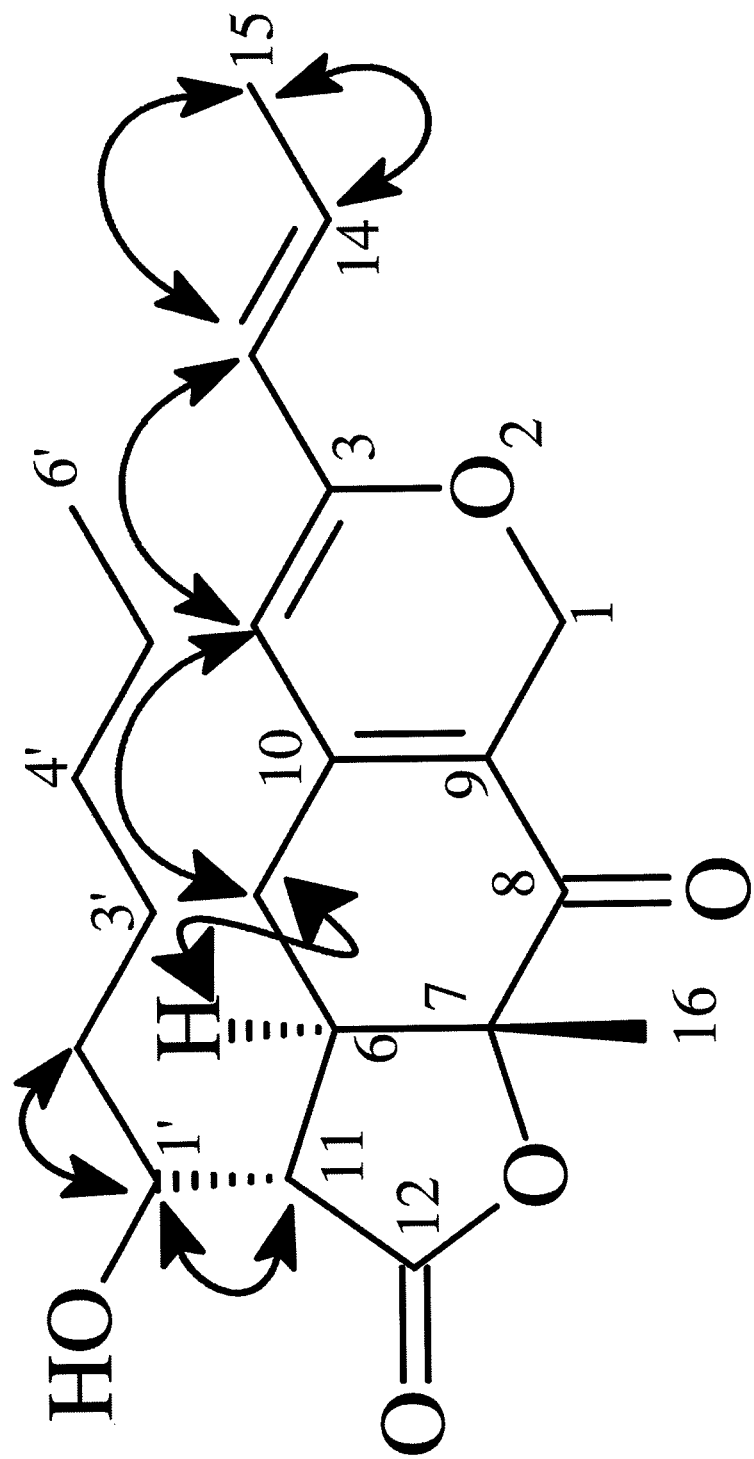
FIG. 2 shows the key NOESY correlations of monascuspiloin.
Figure 3:
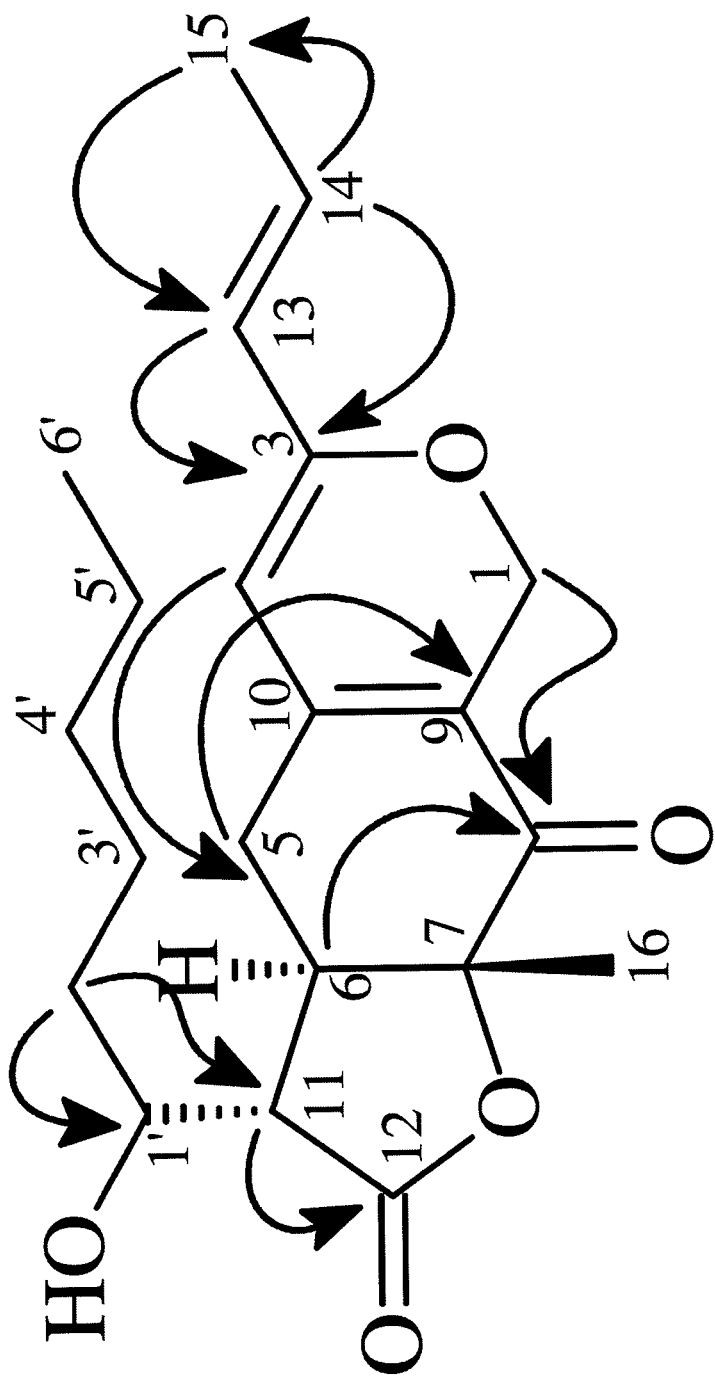
FIG. 3 shows the key HMBC correlations of monascuspiloin.

Compound 1, isolated as yellowish oil, was assigned the molecular formula $C_{21}H_{28}O_5Na$ by ESI-MS ([M+Na]$^+$, m/z 383) and HR-ESI-MS ([M+Na]$^+$, m/z 383.1832). IR (Neat) absorptions were observed at 3400 cm$^{-1}$ and 1738 cm$^{-1}$, pointing to the presence of hydroxyl (OH), and ester carbonyl group (C=O). The UV spectrum ($\lambda_{max}$ (MeOH) nm (log ε)) showed maximum absorption at 230 (4.32) and 388 (4.11) nm, and a bathochromic shift in alkaline solution indicated the presence of a phenol derivative. This was confirmed by the $^1H$ NMR spectrum, which showed one proton at $\delta_H$4.20 (1H, m) assigned to OH-1', which disappeared upon addition of $D_2O$. The $^1H$ NMR spectrum of Compound 1 was similar to that of the known compound, monascin, except that the substitution at C-11 in Compound 1 was an octan-2-ol moiety in place of an octan-2-one group in monascin [0.85 (3H, t, J=5.8 Hz, $CH_3$-6'), 1.23 (4H, m, $CH_2$-4', 5'), 1.50 (2H, m, H-3'), 2.66 (1H, t, J=6.9 Hz, $CH_2$-2' a), and 2.77 (1H, t, J=7.2 Hz, $CH_2$-2' b)]. The structure (see FIG. 1) was further confirmed by $^{13}C$ NMR, DEPT, COSY, NOESY (see FIG. 2), HSQC, and HMBC (see FIG. 3) experiments. Thus, the Compound 1 was determined to be (3S,3aR,9aR)-3a,4-dihydro-3-((S)-1-hydroxyhexyl)-9a-methyl-6-((E)-prop-1-enyl)-3H-furo [3, 2-g] isochromene-2,9(8H,9aH)-dione. Compound 1 was designated monascuspiloin. Monascuspiloin: Yellow oil. $[\alpha]_D^{28}$ –42.1° (c=0.21, $CHCl_3$). IR (Neat) cm$^{-1}$: 3400 (OH), 1738 (C=O). UV $\lambda_{max}$ (MeOH) nm (log ε): 230 (4.32), 388 (4.11).

$^1$H NMR (CDCl$_3$, 400 MHz): 0.90 (3H, t, J=6.8 Hz, CH$_3$-6'), 1.25~1.46 (4H, m, CH$_2$-4', 5'), 1.42 (3H, s, CH$_3$-16), 1.50~1.61 (4H, m, CH$_2$-2', 3'), 1.86 (3H, dd, J=6.8 Hz, CH$_3$-15), 2.53~2.60 (1H, m, H-5), 2.70~2.76 (4H, m, H-5, 11), 2.99~3.06 (4H, m, H-6), 4.20 (1H, m, H-1'), 4.70 (1H, d, J=12.8 Hz, H-1), 5.05 (1H, d, J=12.8 Hz, H-1), 5.28 (1H, s, H-4), 5.89 (1H, br. d, J=12.8 Hz, H-13), 6.49 (1H, m, H-14); $^{13}$C NMR (CDCl$_3$, 100 MHz): 14.0 (6'-CH$_3$), 17.6 (16-CH$_3$), 18.5 (15-CH$_3$), 22.6 (CH$_2$), 25.9 (CH$_2$), 30.9 (CH$_2$), 31.5 (CH$_2$), 34.9 (CH$_2$), 41.2 (C-6), 49.0 (C-11), 63.8 (C-1), 69.4 (C-1'), 83.1 (C-7), 103.3 (C-4), 114.0 (C-9), 124.4 (C-13), 135.3 (C-14), 150.9 (C-10), 160.3 (C-3), 175.1 (C-12), 190.7 (C-8). ESI-MS m/z 383 [M+Na]$^+$. HR-ESI-MS m/z 383.1832 [M+Na]$^+$(calcd for C$_{21}$H$_{28}$O$_5$Na, 363.1834).

Example 3

Alternative Process for Preparing Monascuspiloin

Monascuspiloin can be prepared from the process as depicted in the following scheme:

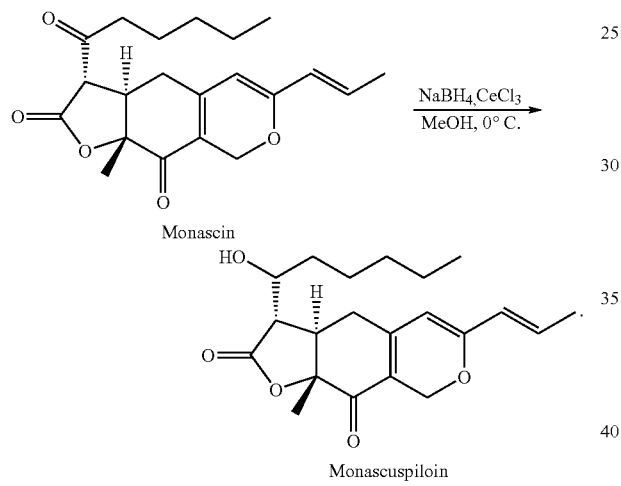

Monascin is a known pigment produced by *Monascus* species and can be prepared by known methods, for example, by the purification method disclosed in Campoy, S. et al., 2006, "Characterization of a hyperpigmenting mutant of *Monascus purpureus* IB 1: identification of two novel pigment chemical structures." *Appl. Microbiol. Biotechnol.* 70: 488-496. Monascuspiloin can be obtained by dissolving purified monascin in methanol with sodium borohydride and reacting at 0° C.

Example 4

The Activity of Red Yeast Rice Extract in the Modulation of an Androgen Receptor Materials and Methods 10 mg of lyophilized ethanol extract of *Monascus ruber* BCRC 31523 obtained from Example 1 were dissolved in 2 mL of DMSO to prepare a 5 mg/mL stock solution. The stock solution was stored at −20° C.

To conduct the assay, the 5 mg/mL stock solution was further diluted with 10% DMSO to prepare 500 µg/mL, and 250 µg/mL diluted samples, and the final concentration of DMSO in the cell culture was 1%.

Figure 4:
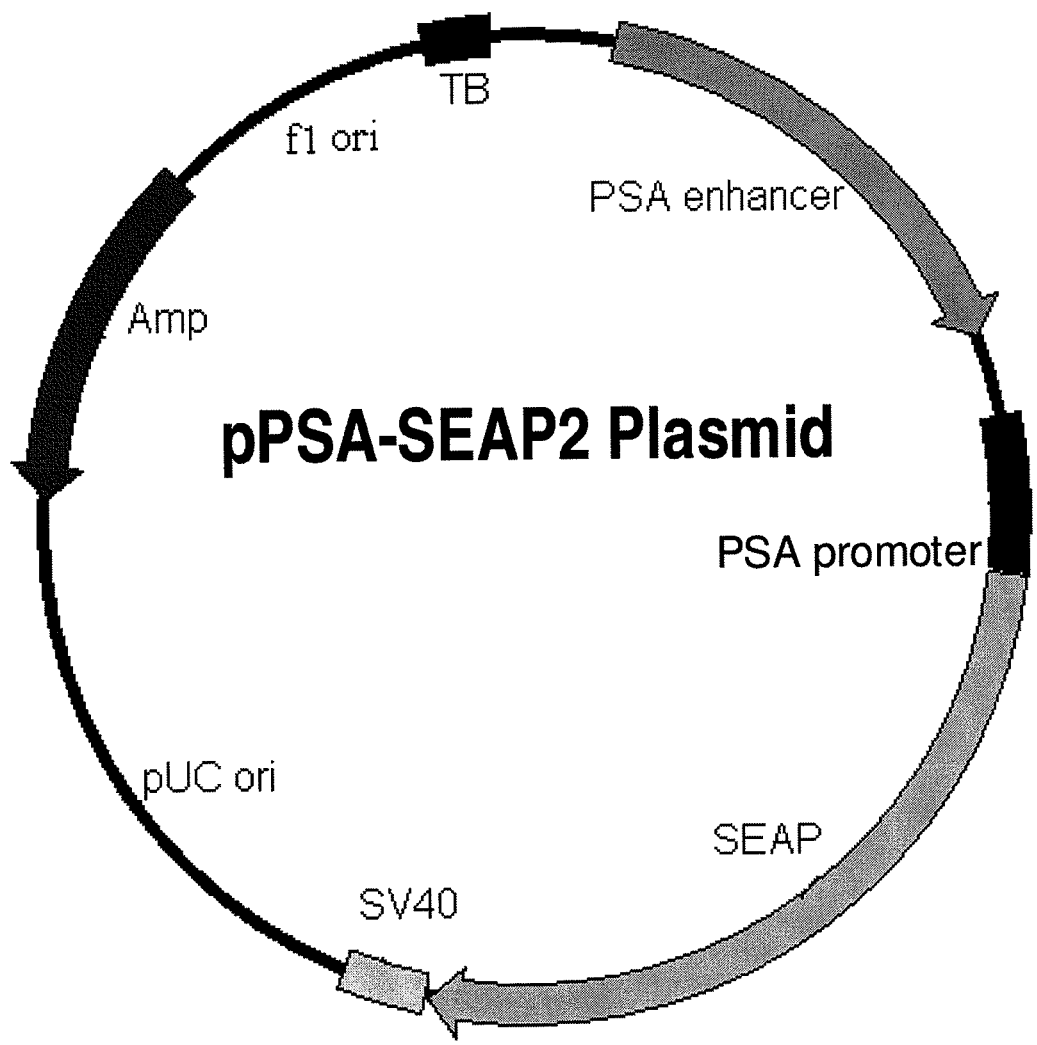
FIG. 4 shows the map of pPSA-SEAP2 plasmid.

Human MDA-MB-453 cells were used in this assay. The cells in the exponential phase of growth (cultured in RPMI 1640 medium (Gibco, USA), 10% FBS) were washed off with 1 ml of 0.05% trypsin, centrifuged and collected in a centrifuge tube. 1×10$^7$ cells were resuspended in 270 µl BES medium (5 mM BES in RPMI 1640 medium) and 8 to 10 µg of pPSA-SEAP2 plasmid (see FIG. 4) were also added to the medium. The cells were electroporated by Gene pulser electroporator (Bio-Rad) at 230 volts and 960µFD capacitance. The electroporated cells were then suspended in 20 ml culture medium (RPMI 1640 medium with 10% FBS) and divided into a 96-well culture plate. The cells were incubated at 37° C. in a 5% CO$_2$ incubator. After 24 hours, the medium was removed and 180 µl of RPMI 1640 medium with 10 nM 5α-dihydrotestosterone (DHT) and 20 µl each of the diluted samples were added to each well. The medium was mixed and incubated at 37° C. in a 5% CO$_2$ incubator for 48 hours.

25 µl of media were retrieved from each cell of the 96-well plate and heated in a 65° C. water bath for 30 minutes. The media were then treated by Phospha-Light™ assay system (Applied Biosystem) in order to detect the secreted alkaline phosphatase (SEAP) reporter protein. The intensity of luminescence was detected by Victor™ Light luminescence counter to determine the activity of the samples in the modulation of the androgen receptor.

Results

Figure 5:
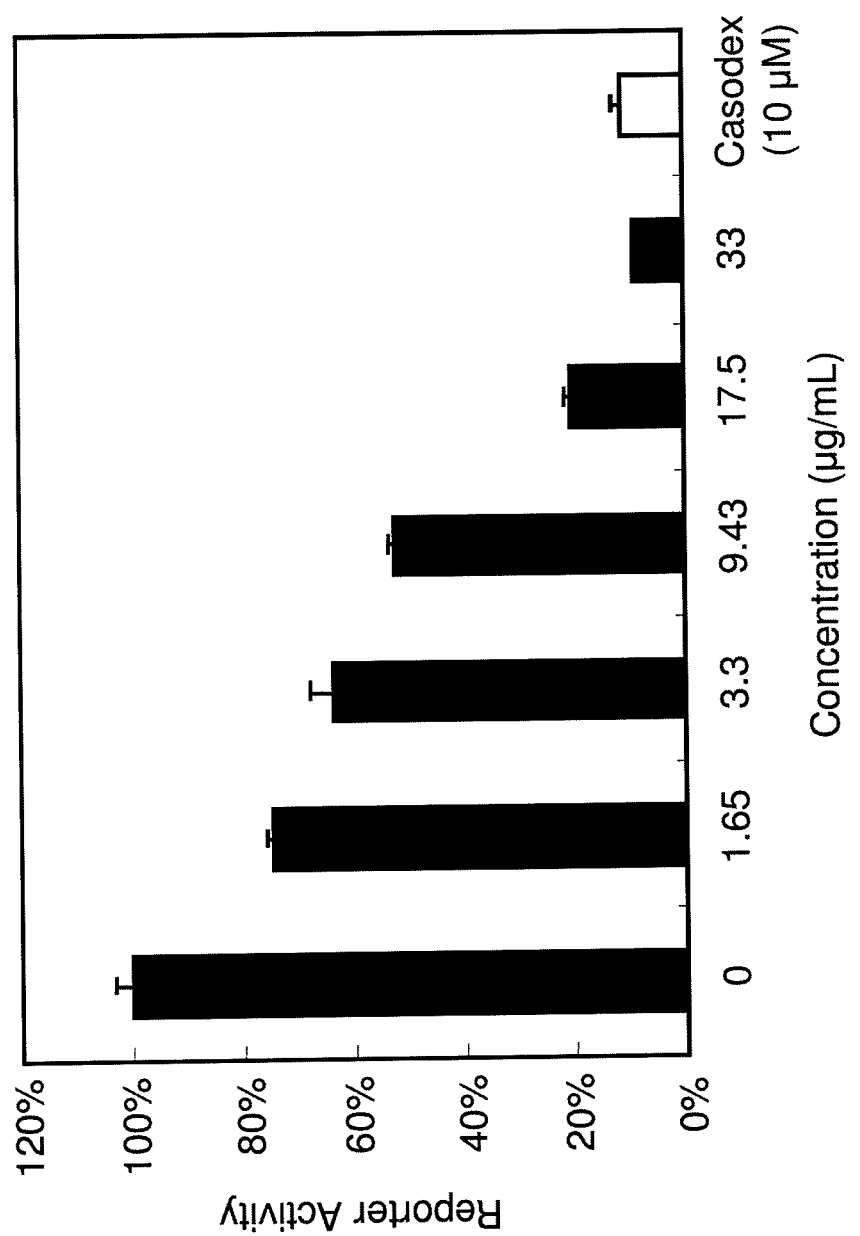
FIG. 5 shows the activity of the extract of red yeast rice in the suppression of an androgen receptor.

As shown in FIG. 5, the red yeast ferment extract has an antagonistic efficacy on the DHT-activated androgen receptor, and the antagonistic efficacy is positive correlated with the concentration of the extract. The activation of the androgen receptor by DHT can be almost completely inhibited by increasing the concentration of the extract. At the final concentration of 33 µg/ml, the inhibitory activity in the expression of the reporter gene is higher than 90%.

Example 5

The Activity of Monascuspiloin in the Modulation of an Androgen Receptor Materials and Methods Monascuspiloin was dissolved in DMSO to prepare a 250 µM monascuspiloin stock solution. The stock solution was stored at −20° C.

To conduct the assay, the 250 µM monascuspiloin solution was further diluted with 10% DMSO to prepare 25 µM, and 5 µM monascuspiloin samples, and the final concentration of DMSO in the cell culture was 1%.

Human MDA-MB-453 cells were used in this assay. The cells in the exponential phase of growth (cultured in RPMI 1640 medium (Gibco), 10% FBS) were washed off with 1 ml of 0.05% trypsin, centrifuged and collected in a centrifuge tube. 1×10$^7$ cells were resuspended in 270 µl BES medium (5 mM BES in RPMI 1640 medium) and 8 to 10 µg of pPSA-SEAP2 plasmid (see FIG. 4) were also added to the medium. The cells were electroporated by Gene puller electroporator (Bio-Rad) at 230 volts and 960 µFD capacitance. The electroporated cells were then suspended in 20 ml culture medium (RPMI 1640 medium with 10% FBS) and divided into a 96-well culture plate. The cells were incubated at 37° C. in a 5% CO$_2$ incubator. After 24 hours, the medium was removed and 180 µl of RPMI 1640 medium with 10 nM 5α-dihydrotestosterone (DHT) and 20 µl each of the monascuspiloin samples were added to each well. The medium was mixed and incubated at 37° C. in a 5% CO$_2$ incubator for 48 hours.

Figure 6:
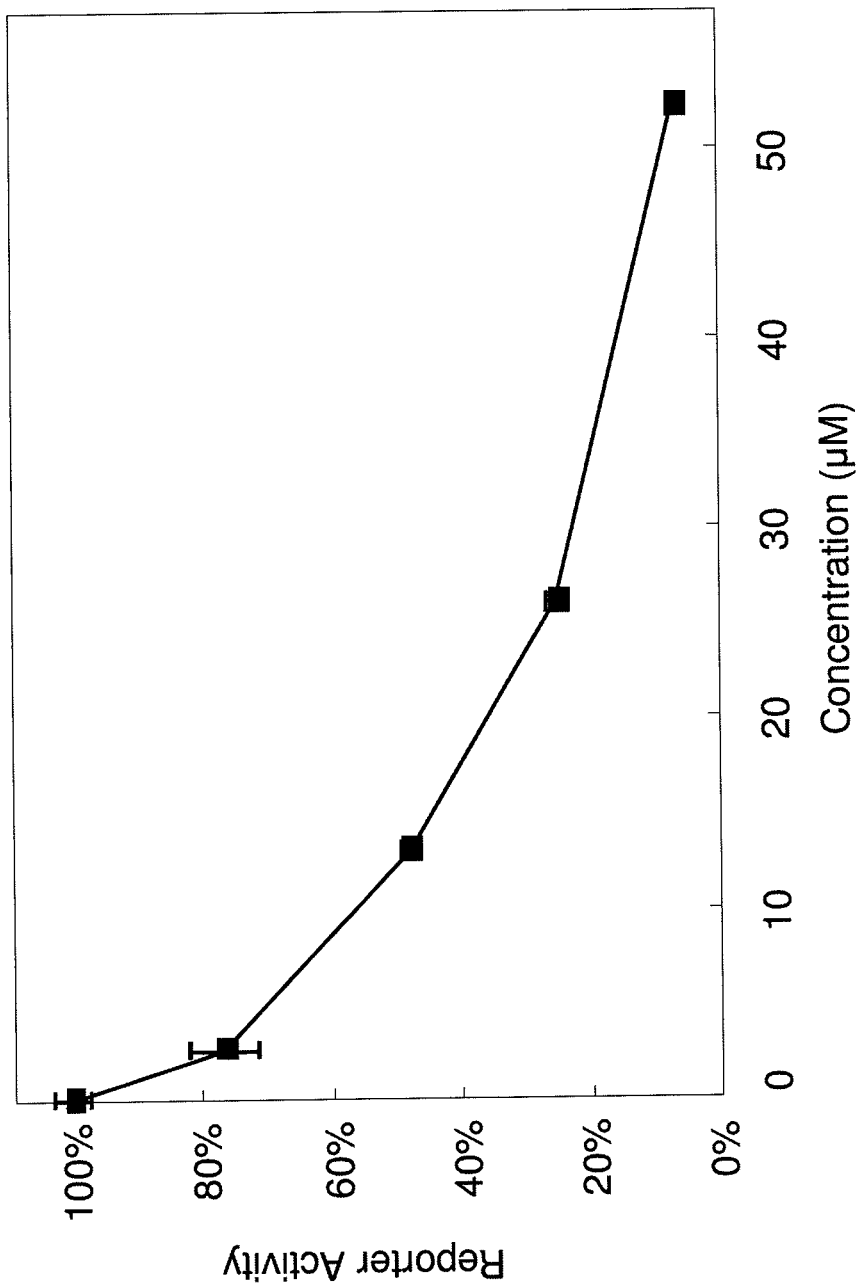
FIG. 6 shows the activity of monascuspiloin in the suppression of an androgen receptor.

25 µl of media were retrieved from each cell of the 96-well plate and heated in a 65° C. water bath for 30 minutes. The media were then treated by Phospha-Light™ assay system (Applied Biosystem) in order to detect the secreted alkaline phosphatase (SEAP) reporter protein. The intensity of luminescence was detected by Victor™ Light luminescence counter to determine the activity of the samples in the modulation of the androgen receptor.
Results As shown in FIG. 6, monascuspiloin can inhibit the activity of an androgen receptor and the inhibitory efficacy is positive correlated with the concentration of monascuspiloin. The $IC_{50}$ of monascuspiloin for the inhibition of the activation of the androgen receptor is about 12 μM.

Example 6

The Activity of Monascuspiloin in the Modulation of Other Nuclear Hormone Receptors Materials and Methods Monasuspiloin was dissolved in DMSO to prepare a 250 μM monasuspiloin stock solution. The stock solution was stored at −20° C.

To conduct the assays, the 250 μM monasuspiloin solution was further diluted with 10% DMSO to prepare 25 μM, and 5 μM monascuspiloin samples, and the final concentration of DMSO in the cell culture was 1%.

Figure 7:
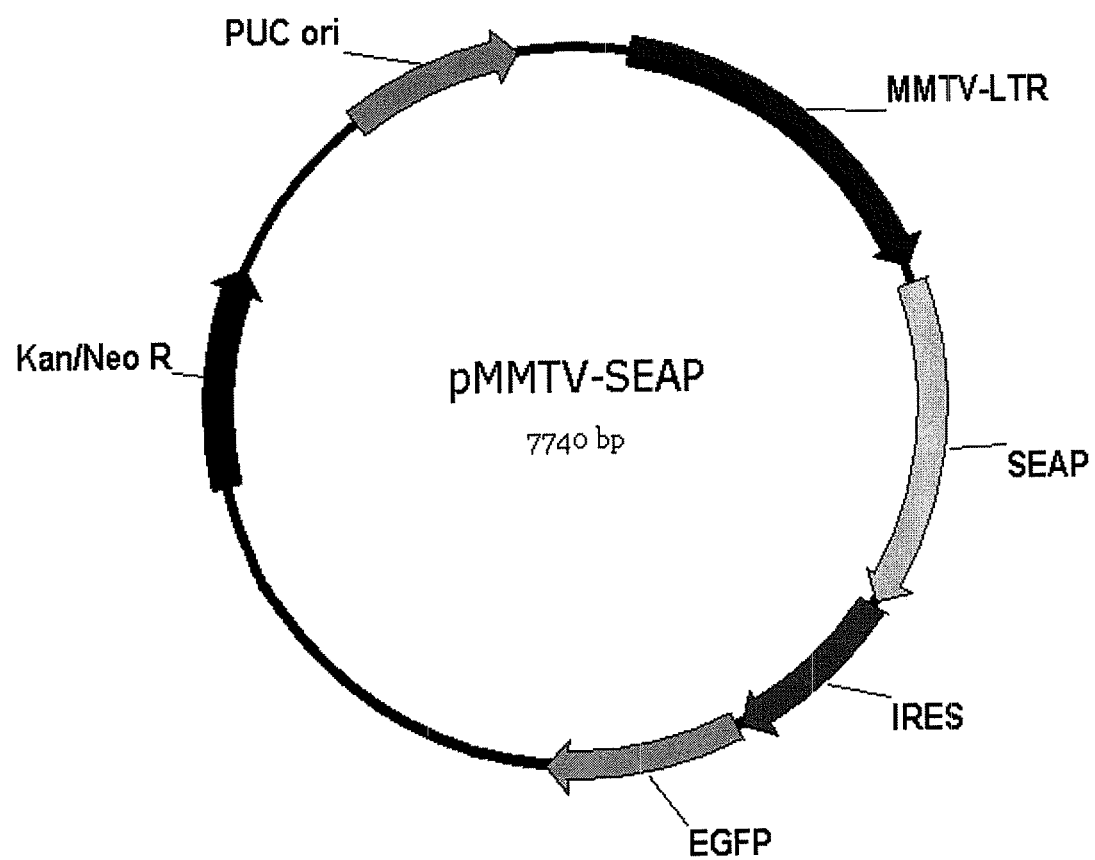
FIG. 7 shows the map of pMMTV-SEAP plasmid.
Figure 8:
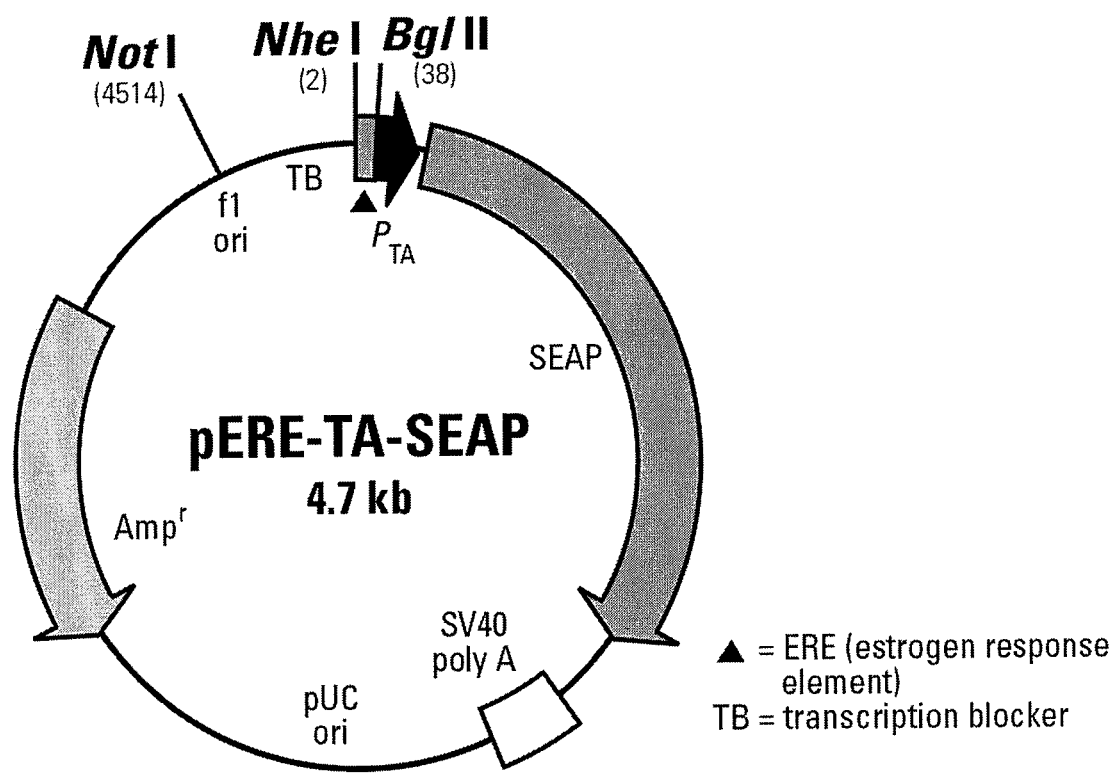
FIG. 8 shows the map of pERE-TA-SEAP plasmid.

The cell line used in glucocorticoid receptor (GR) assay was human A-549 cells (cultured in Ham's F12K medium (Gibco, USA), 10% FBS), the cell line used in progesterone receptor (PR) assay was human T-47D cells (cultured in RPMI 1640 medium (Gibco, USA), 10% FBS), and the cell line used in estrogen receptor (ER) assay was human MCF$_7$ cells (cultured in MEM medium (Gibco, USA), 10% FBS). The cells in the exponential phase of growth were washed off with 1 ml of 0.05% trypsin, centrifuged and collected in a centrifuge tube. 1×10$^7$ cells were resuspended in 270 μl BES medium (5 mM BES in medium) and 8 to 10 μg of plasmid [pMMTV-SEAP plasmid was used for GR and PR (see FIG. 7), and pTA-ERE-SEAP plasmid (Clontech, USA) was used for ER (see FIG. 8)] were also added to the medium. The cells were electroporated by Gene pulser electroporator (Bio-Rad) at 230 volts and 960 μFD capacitance. The electroporated cells were then suspended in 20 ml culture medium (MEM medium with 10% FBS) and divided into a 96-well culture plate. The cells were incubated at 37° C. in a 5% $CO_2$ incubator. After 24 hours, the medium was removed and 180 μl of medium with 10 nM of corresponding hormone (Dexmethasone for GR, Progestin for PR, and Estradiol for ER) and 20 μl each of the monascuspiloin samples were added to each well. The medium was mixed and incubated at 37° C. in a 5% $CO_2$ incubator for 48 hours.
Results Table 1 summarized the $IC_{50}$ of monascuspiloin for inhibiting the activation of an androgen receptor, a glucocorticoid receptor, a progesterone receptor and an estrogen receptor.

TABLE 1

The $IC_{50}$ of monascuspiloin against nuclear hormone receptors

| Nuclear Hormone Receptor | $IC_{50}$ |
|---|---|
| Androgen Receptor | 12 μM |
| Glucocorticoid Receptor | 35 μM |
| Progesterone Receptor | 27 μM |
| Estrogen Receptor | 16 μM |

It can be learnt from Table 1 that in addition to androgen receptors, monascuspiloin can inhibit other nuclear hormone receptors, particularly steroid hormone receptors.

Example 7

Figure 9:
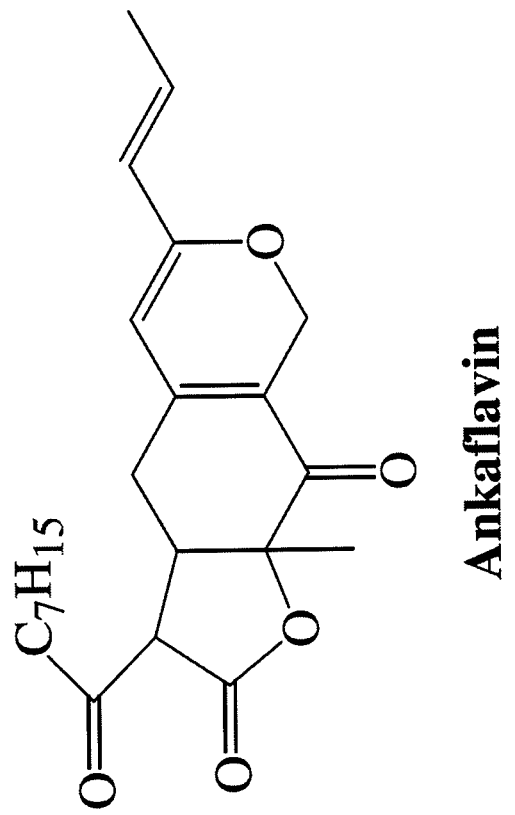
FIG. 9 shows the structures of monascin and ankaflavin.
Figure 9:
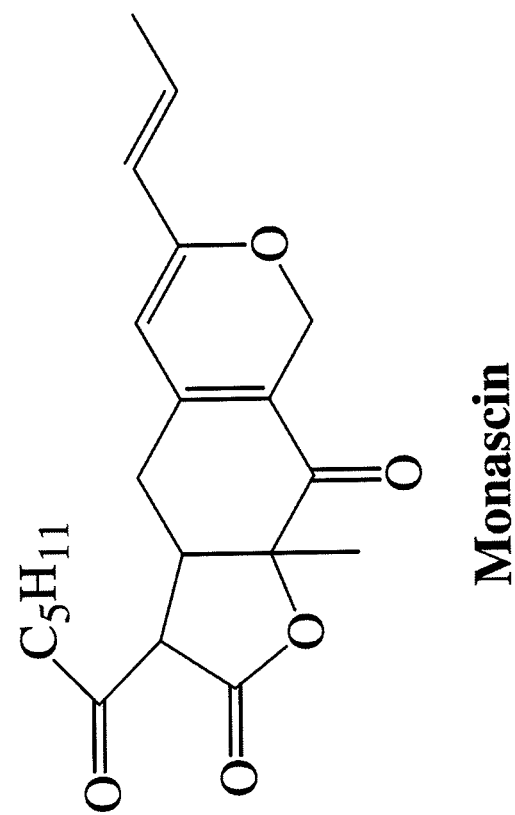

The Activity of Other Azaphilone Compounds in the Modulation of an Androgen Receptor Materials and Methods In order to test whether other azaphilone compounds have the same inhibitory activity as that of monascuspiloin, two red yeast pigments, monascin and ankaflavin, were used in this assay. Monascin and ankaflavin are both metabolites produced by *Monascus* sp. and their structures are shown in FIG. 9.

Monascin and ankaflavin were dissolved in DMSO to prepare 250 μM stock solutions. The stock solutions were stored at −20° C.

To conduct the assay, the 250 μM stock solutions were further diluted with 10% DMSO to prepare 25 μM, and 5 μM monascin or ankaflavin samples, and the final concentration of DMSO in the cell culture was 1%.

Human MDA-MB-453 cells were used in this assay. The cells in the exponential phase of growth (cultured in RPMI 1640 medium (Gibco), 10% FBS) were washed off with 1 ml of 0.05% trypsin, centrifuged and collected in a centrifuge tube. 1×10$^7$ cells were resuspended in 270 μl BES medium (5 mM BES in RPMI 1640 medium) and 8 to 10 μg of pPSA-SEAP2 plasmid (see FIG. 4) were also added to the medium. The cells were electroporated by Gene pulser electroporator (Bio-Rad) at 230 volts and 960 μFD capacitance. The electroporated cells were then suspended in 20 ml culture medium (RPMI 1640 medium with 10% FBS) and divided into a 96-well culture plate. The cells were incubated at 37° C. in a 5% $CO_2$ incubator. After 24 hours, the medium was removed and 180 μl of RPMI 1640 medium with 10 nM 5α-dihydrotestosterone (DHT) and 20 μl each of the monascuspiloin samples were added to each well. The medium was mixed and incubated at 37° C. in a 5% $CO_2$ incubator for 48 hours.

Figure 10:
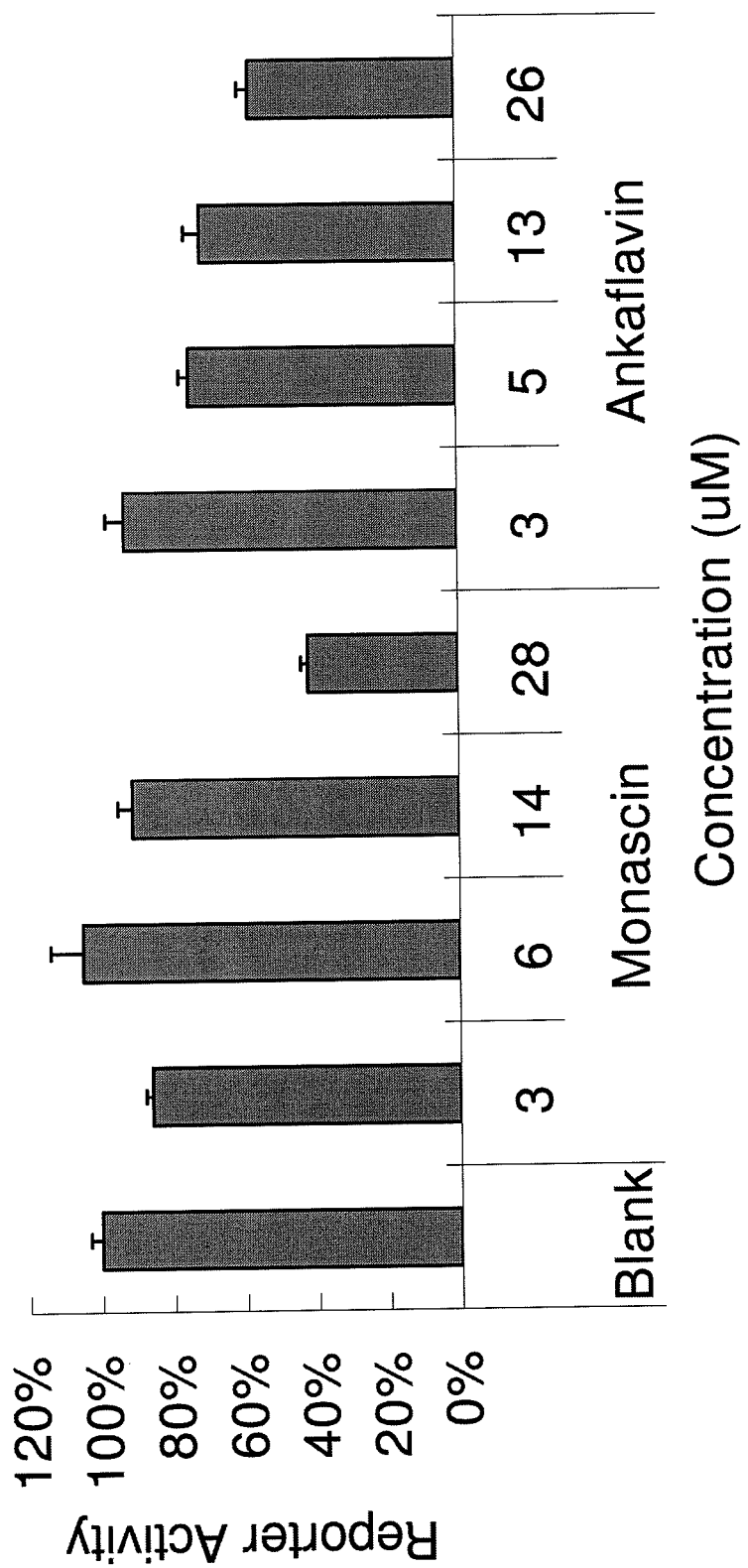
FIG. 10 shows the activity of monascin and ankaflavin in the suppression of an androgen receptor.

25 μl of media were retrieved from each cell of the 96-well plate and heated in a 65° C. water bath for 30 minutes. The media were then treated by Phospha-Light™ assay system (Applied Biosystem) in order to detect the secreted alkaline phosphatase (SEAP) reporter protein. The intensity of luminescence was detected by Victor™ Light luminescence counter to determine the activity of the samples in the modulation of the androgen receptor.
Results As shown in FIG. 10, both monascin and ankaflavin can inhibit the activity of an androgen receptor to different degrees. At the concentration of 28 monascin inhibited 55% of the reporter activity. At the concentration of 26 μM, ankaflavin inhibited 41% of the reporter activity. The results suggest that azaphilone compounds are capable of inhibiting the activity of an androgen receptor.

Example 8

The Activity of Monascuspiloin in the Inhibition of 5α-Reductase

Materials and Methods

Monascuspiloin was dissolved in 100% ethanol. To evaluate the activity of monascuspiloin in the inhibition of 5α-reductase, four monascuspiloin solutions having the concentration of 3.1, 6.4, 9.3 and 18.6 mM were prepared.

The method for detecting the inhibition of 5α-reductase activity is described in Cabeza et al., 2001 (Cabeza M, Heuze I, Bratoeff E, Ramirez E, Martinez R. 2001. Evaluation of new pregnane derivatives as 5alpha-reductase inhibitor. Chem Pharm Bull (Tokyo) 49(5):525-30.). $1 \times 10^7$ *Penicillium decumbens* BCRC 31695 spores were inoculated in a 250 ml Erlenmeyer flask containing 50 ml of potato dextrose broth (PDB) medium (Difco, USA) and incubated at 25° C. for 1 day. 2 ml of the fermented broth was divided into a 24-well plate. 7.5 μl of testosterone (concentration: 20 mg/ml) and 20 μl of monascuspiloin solution were added into each well (the final concentrations of monascuspiloin in the wells were 62, 128, 186 and 372 μM). The culture was incubated at 25° C. for 4 days, and the fermented broth in each well was extracted with 3 ml EtOAc twice. The EtOAc-soluble fractions were vacuum-dried to remove EtOAc. The residues were re-dissolved in 1 ml ethanol and the amounts of testosterone and dihydro-testosterone were analyzed by HPLC.

The method of evaluating the inhibition of 5α-reductase activity is described in Matsuda et al., 2001 (Matsuda H, Yamazaki M, Matsuo K, Asanuma Y, Kubo M. 2001. Anti-androgenic activity of Myricae Cortex—isolation of active constituents from bark of Myrica rubra. Biol Pharm Bull 24(3):259-63.). The inhibitory activity is calculated by the following equation:

$$\text{Inhibitory activity}(\%) = \frac{(T \text{ of } sample^{after} - T \text{ of } control^{after}) \times 100}{(T \text{ of } control^{before} - T \text{ of } control^{after})}$$

Figure 11:
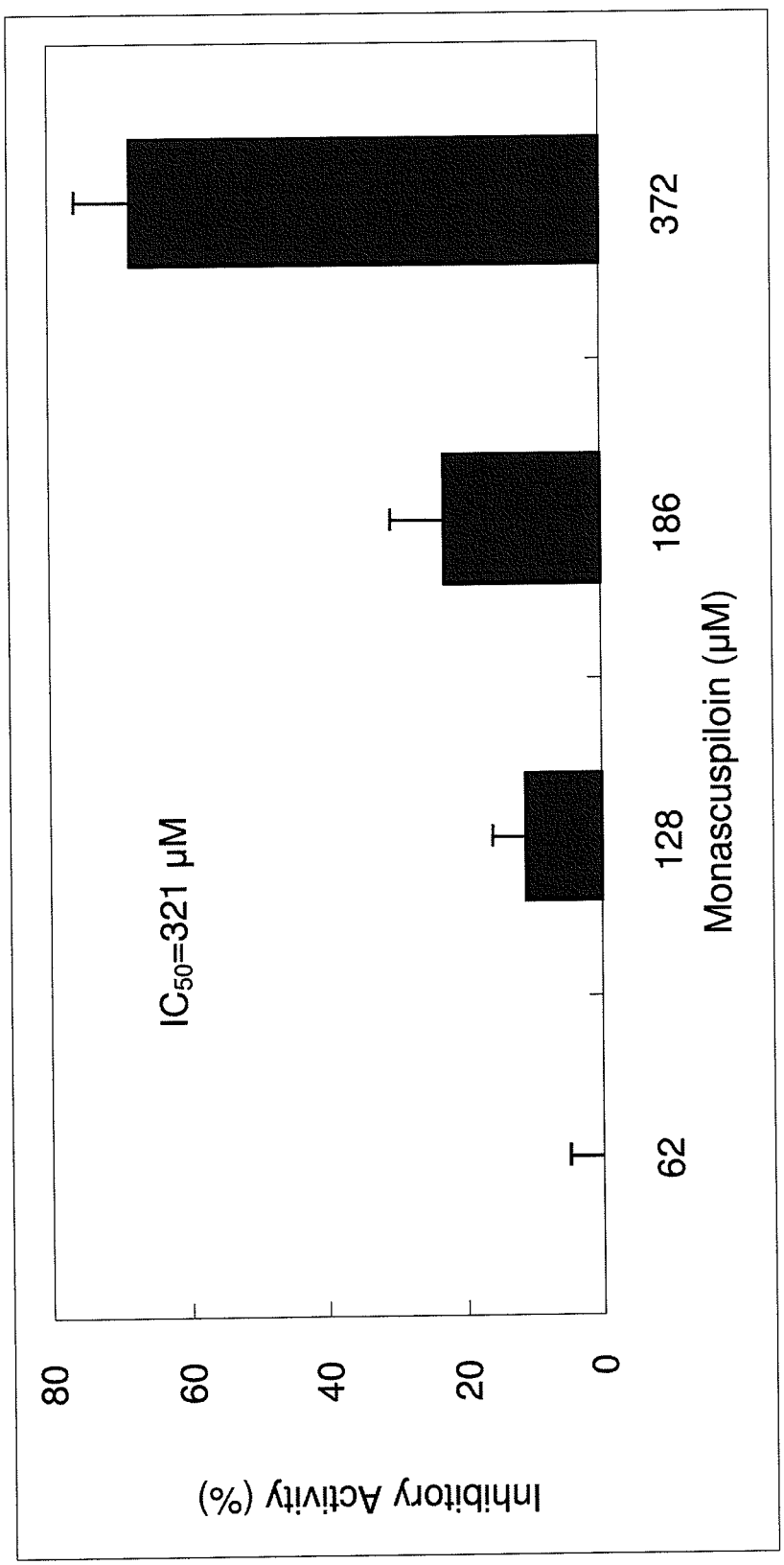
FIG. 11 shows the activity of monascuspiloin in the inhibition of the conversion of testosterone into dihydro-testosterone by the 5-α-reductase purified from *Penicillium decumbens*.

T: testosterone
Control: 100% ethanol
Before: the amount of testosterone extracted from the sample obtained at 0 hour
After: the amount of testosterone extracted from the sample obtained after 4 days Results 5α-reductase is the enzyme that converts testosterone into dihydro-testosterone. As shown in FIG. 11, monascuspiloin is capable of inhibiting the conversion of testosterone into dihydro-testosterone by the 5-α-reductase purified from *Penicillium decumbens*. The results showed that monascuspiloin can inhibit the activity of 5α-reductase and the $IC_{50}$ is about 321 μM.

Example 9

The Anti-Cancer Cell Activity of Monascuspiloin

Materials and Methods

The survive rate of cell was determined by the MTT (3-(4, 5-dimethyl-2-thiazolyl)-2,5-diphenyl tetrazolium bromide) method. Nine cell lines were used in the test, which included three different human prostate cancer cell lines, i.e., LNCap.FGC, DU145 and PC-3, wherein LNCap.FGC is androgen dependent from lymph nodes metastatic site, and DU145 and PC-3 are androgen independent from prostate cancer metastasizing to brain and bone, respectively; and six other human cancer cell lines, i.e., human lung fibroblast MRC-5, human breast adenocarcinoma MCF-7, human hepatoblastoma HepG2, human gastric adenocarcinoma AGS, human cervical epithelioid carcinoma HeLa, and human embryonic kidney 293 cells. The cell lines used are shown in Table 2.

TABLE 2

| Cell Lines | | BCRC* | cells/well** |
|---|---|---|---|
| Prostate cancer cell | LNCap.FGC | 60088 | 5000 |
| Prostate cancer cell | DU145 | 60348 | 3500 |
| Prostate cancer cell | PC-3 | 60122 | 3500 |
| Normal lung fibroblast | MRC-5 | 60025 | 5000 |
| Breast cancer cell | MCF-7 | 60436 | 3000 |
| Liver cancer cell | HepG2 | 60102 | 3000 |
| Stomach cancer cell | AGS | 60005 | 3000 |
| Cervical cancer cell | HeLa | 60023 | 1500 |
| Kidney cell | HEK 293 | 60019 | 3000 |

*Accession numbers of BCRC.
**Inoculation amount of cell in each well of a 96-well plate.

Cell lines were respectively incubated in the media and conditions shown in the website of the Biosource Collection and Research Center (BCRC) of the Food Industry Research and Development Institute (FIRDI). Briefly, LNCap.FGC was incubated in the medium containing 90% RPMI 1640, 4.5 g/L glucose, 10 mM HEPES, 1.0 mM sodium pyruvate, and 10% FBS; PC-3 was incubated in the medium containing 93% Ham's F12K medium and 7% FBS; AGS was incubated in the medium containing 90% Ham's F12K medium and 10% FBS; and the other six cell lines were incubated in the medium containing 90% MEM, 10 mM sodium pyruvate and 10% FBS. Frozen cells were thawed in a 37° C. water bath, and then activated in T25 containing 15 ml of medium, at 37° C. in a 5% $CO_2$ incubator. The cells were further subcultured at least once. When cultured cells reached 70-80% confluency, cells were washed with phosphate buffered saline (PBS) two times, then the cells were treated with trypsin-EDTA solution at 37° C. When the cells came off the wall of the container, the cells were diluted with fresh culture medium to the desired concentration. 180 μl of the diluted cell culture of each cell line were added to the well of a 96-well plate. The cell number of each cell line added is shown in Table 2. The 96-well plate was incubated overnight at 37° C. in a $CO_2$ incubator.

Monascuspiloin, Casodex (Bicalutamide, AstraZeneca, UK) and Flutamide (F9397, Sigma-Aldrich, USA) were dissolved in DMSO to prepare stock solutions of 52.2 mM, 10 mM and 18.7 mM, respectively. To conduct the MTT assay, each stock solution was further diluted to prepare 200 μM, 100 μM, 50 μM, and 10 μM samples, and the concentration of DMSO was 10%. 20 μl of each sample were added to the cell culture in the 96-well plate. Each sample was assayed in quadruplet. In the cell cultures, the final concentrations of the samples were 20 μM, 10 M, 5 μM, and 1 μM, respectively, and the final concentration of DMSO in the media was 1%. The control was the cell culture containing 1% DMSO. The cell cultures treated with the samples were incubated at 37° C. in a $CO_2$ incubator for 72 hours. Then, 20 μl of 5 mg/ml MTT were added to the culture and incubated for 4 hours at 37° C. in a CO2 incubator. The supernatant of the culture was removed. 100 μl DMSO were added to each well and the plate was shaken for 5 minutes. The O.D. values of the cells were determined by an enzymatic analyzer at a wave length of 540 nm (reference wave length was 690 nm). The method of evaluating the activity of MTT is described in Alley et al. 1988 (Alley, M. C., Scudiero, D. A., Monks, A., Hursey, M. L., Czerwinski, M. J., Fine, D. L., Abbott, B. J., Mayo, J. G., Shoemaker, R. H., and Boyd, M. R. 1988. Feasibility of Drug Screening with Panels of Human Tumor Cell Lines Using a Microculture Tetrazolium Assay. Cancer Research, 48: 589-601). The activity is calculated by the following equation:

$$MTT\ activity(\%) = \frac{O.D.\ value\ of\ test\ group}{O.D.\ value\ of\ control} \times 100\%$$

Results

Figure 12:
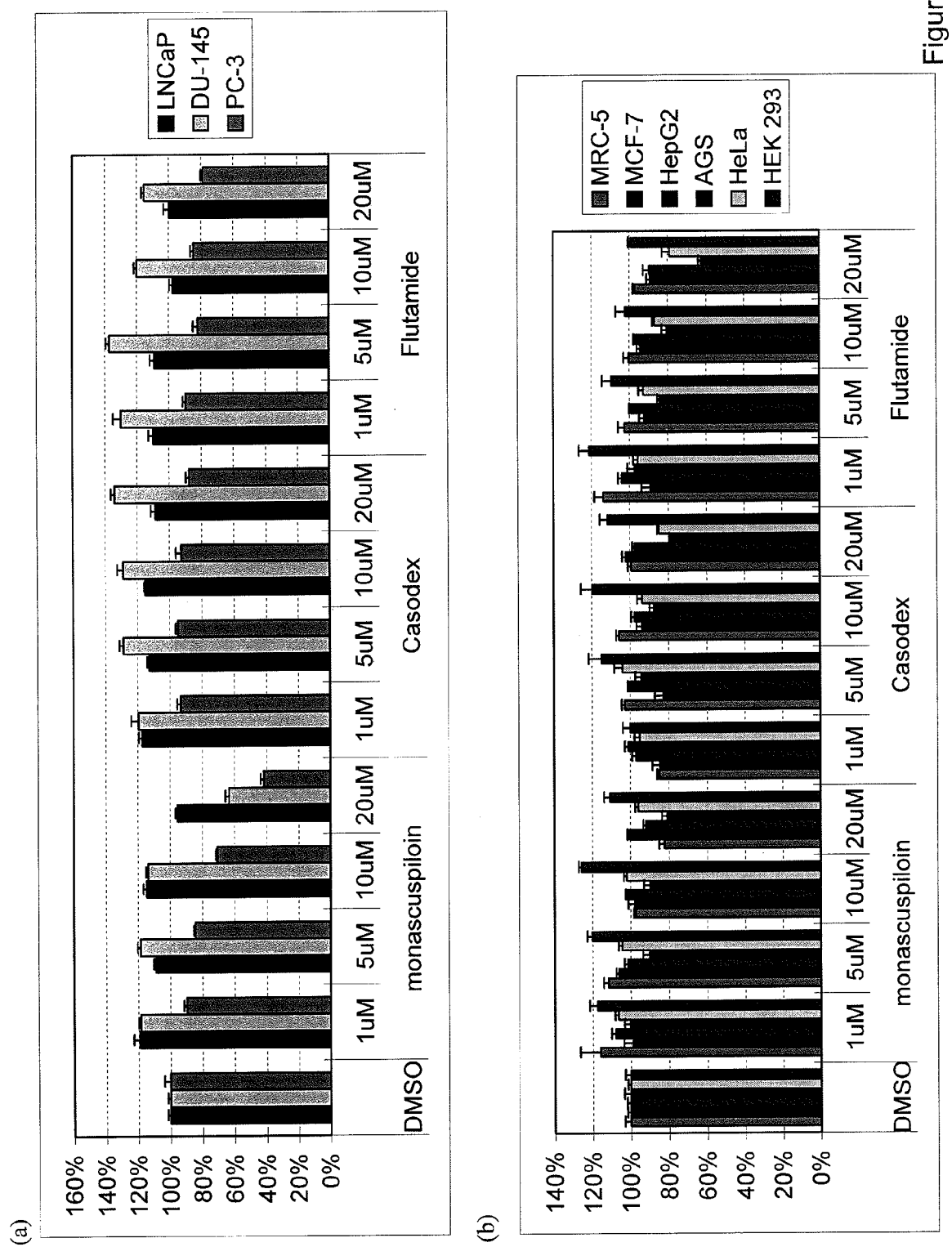
FIG. 12 shows the MTT analysis results: (a) is the results of LNCap.FGC cells, DU145 cells and PC-3 cells, and (b) is the results of human lung fibroblast MRC-5, human breast adenocarcinoma MCF-7, human hepatoblastoma HepG2, human gastric adenocarcinoma AGS, human cervical epithelioid carcinoma HeLa, and human embryonic kidney 293 cells.

As shown in FIGS. 12 (a) and (b), monascuspiloin is capable of inhibiting the growth of the male hormone independent prostate cancer cell lines DU145 and PC-3 with the $IC_{50}$ of 27.2 µM and 17.3 µM, respectively; but does not have a significant cytotoxic effect on prostate cancer cell line LNCap.FGC and the other 6 non-human-prostate-cancer cell lines.

Example 10

The Effect of Monascuspiloin in the Inhibition of Secretion of Prostate Specific Antigen (PSA)

Materials and Methods

Prostate specific antigen (PSA) is a protein secreted by the epidermal cells of prostate. PSA facilitates semen liquification and presents in male serum in minute amount. In the serum of male subjects suffering from prostate cancer, benign prostatic hyperplasia or prostatic infection, the quantity of PSA presented in serum may increase. Therefore, PSA is so far the most valuable marker in screening and diagnosing prostate tumors. PSA also plays an important role in determining a cancer's stage of development and evaluating the effect of treatment. The amounts of PSA were determined by using Prostate Specific Antigen ELISA kit (Cat. No. BQ067T, Bio Quant, USA). After separately incubating LNCap.FGC cells in either basal medium (containing 90% RPMI 1640, 4.5 g/L glucose, 10 mM HEPES, 1.0 mM sodium pyruvate, and 10% FBS), dihydrotestosterone (DHT) medium (basal medium and 5 nM DHT), or monascuspiloin medium (DHT medium and 5 µM, 10 µM or 20 µM monascuspiloin) for 48 hours, the cultures were retrieved. 50 µl of each of the retrieved culture media and 50 µl of each of the standard PSA of 0, 2, 4, 8, 25, and 50 ng/ml were added to the wells of a 96-well plate, respectively. Then, 50 µl assay buffer was further added to the wells, and the plate was incubated at room temperature in the dark for 30 minutes. The supernatant was removed and the wells were washed three times with 300 µl wash buffer. 100 µl Enzyme Conjugate was added to each well, and the plate was incubated at room temperature in the dark for 30 minutes. The supernatant was removed and the wells and washed three times with 300 µl wash buffer. 100 µl TMB substrate was added to each well, and the plate was incubated at room temperature in the dark for 15 minutes. 50 µl stop solution was added to each well, and the plate was gently shaken for 30 seconds to ensure that the color of the solution in the well turned completely yellow. Within 15 minutes after completion of the previous step, the wells were examined by a ELISA Reader at 450 nm.

Results

As shown in Table 3, the concentration of PSA measured in the basal medium is 4.21 ng/ml, and that in the DHT medium increases to 12.61 ng/ml. Therefore, DHT can induce the production of PSA. However, monascuspiloin at a concentration of 20 µM can effectively inhibit the production of PSA induced by DHT at 43%. This indicates that to monascuspiloin is an antagonist against the secretion of PSA induced by DHT.

TABLE 3

| Culture media | PSA concentration (ng/ml) |
| --- | --- |
| Complete basal medium | 4.21 |
| Dihydrotestosterone (DHT) 5 nM | 12.61 |
| DHT 5 nM + Monascuspiloin 5 µM | 10.27 |
| DHT 5 nM + Monascuspiloin 10 µM | 9.71 |
| DHT 5 nM + Monascuspiloin 25 µM | 8.77 |

While the present invention has been described in conjunction with the specific embodiments set forth above, many alternatives thereto and modifications and variations thereof will be apparent to those of ordinary skill in the art. All such alternatives, modifications and variations are regarded as falling within the scope of the present invention.

What is claimed is:

1. A method comprising treating a disease or disorder related to androgen receptor activity in a subject, which comprises administering to said subject an effective amount of a compound which is (3S,3aR,9aR)-3a,4-dihydro-3-(S)-1-hydroxyhexyl)-9a-methyl-6-((E)-prop-1-enyl)-3H-furo[3,2-g]isochromene-2,9(8H,9aH)-dione or a pharmaceutically acceptable salt thereof, or a purified extract from a red yeast rice fermentation product of *Monascus* spp. comprising the compound, wherein the disease or disorder is selected from the group consisting of prostatic hyperplasia, androgen-dependent alopecia, hirsutism and acne.

2. The method of claim 1, wherein the disease or disorder is acne.

3. The method of claim 1, wherein the disease or disorder is treated by administering the compound to the subject.

4. The method of claim 1, wherein the disease or disorder is treated by administering the extract to the subject, wherein the purified extract does not comprise azaphilone compounds of the red yeast rice fermentation product of *Monascus* spp. other than the compound.

5. The method of claim 4, wherein the extract is the purified extract of a red yeast rice fermentation product of *Monascus* spp that is produced by extracting the fermentation product with ethanol and purifying the ethanol extract with HPLC to obtain the compound.

6. The method of claim 1, wherein the disease or disorder is prostatic hyperplasia.

7. The method of claim 1, wherein the disease or disorder is androgen-dependent alopecia.

8. The method of claim 1, wherein the disease or disorder is hirsutism.

9. The method of claim 1, wherein the disease or disorder is treated by administering the pharmaceutically acceptable salt to the subject.

* * * * *